United States Patent [19]

Cho et al.

[11] Patent Number: 4,920,145

[45] Date of Patent: Apr. 24, 1990

[54] WATER-SOLUBLE COMPLEXES OF WATER-INSOLUBLE PHARMACEUTICAL COMPOUNDS AND PREPARATION THEREOF

[75] Inventors: James R. Cho, Oakland; Terry E. Smith, Morristown; Ian W. Cottrell, Kinnelon, all of N.J.

[73] Assignee: GAF Chemical Corporation, Wayne, N.J.

[21] Appl. No.: 161,881

[22] Filed: Feb. 29, 1988

[51] Int. Cl.$^5$ .................. A61K 31/405; A61K 31/41; C07D 209/28; C07D 207/267
[52] U.S. Cl. .................................. 514/420; 514/471; 514/635; 514/646; 548/500; 548/543
[58] Field of Search ...................... 548/496, 500, 543; 514/646, 471, 635, 420

[56] References Cited

U.S. PATENT DOCUMENTS 4,663,348  7/1985  Chafetz .......................... 514/471
4,831,194  5/1989  Kreidl et al. ..................... 514/646

FOREIGN PATENT DOCUMENTS 2805248  8/1978  Fed. Rep. of Germany ...... 514/635
0144316  8/1983  Japan .

OTHER PUBLICATIONS

Colwell et al., J. of Med. Chem., 17, pp. 142–144, (1974).

Primary Examiner—David B. Springer
Attorney, Agent, or Firm—Jules E. Goldberg; Marilyn J. Maue; Joshua J. Ward

[57] ABSTRACT

A method for increasing the water-solubility of highly insoluble organic compounds by forming a novel complex product from the reaction between the organic compound and an oligomer of vinylpyrrolidone. The complex is highly stable and results in solubilities of the organic compounds in excess of 25-fold.

18 Claims, No Drawings

WATER-SOLUBLE COMPLEXES OF WATER-INSOLUBLE PHARMACEUTICAL COMPOUNDS AND PREPARATION THEREOF

BACKGROUND OF THE INVENTION

A major difficulty encountered with many organic compounds, particularly those of higher molecular weight and/or those having relatively complicated formulas, such as, pharmaceuticals, is that they are highly insoluble in water. This places significant limitations on the potential uses of these materials. For example, for those organic compounds which are used for industrial purposes, normally, a wide variety of organic solvents can be used. However, such solvents often present problems from the standpoint of cost and/or environmental impact. As a result, normally associated with the use of such organic solvents is the problem of their recovery so as to minimize the cost involved with their use, or their neutralization in the sense that the solvents no longer present an environmental or health hazard to humans or animals.

It is thus desirable that such compounds, rather than being utilized in organic solvents, be dissolved in water as the solvent. However, because of the nature of the organic compounds, it is often impossible to achieve a sufficiently high concentration of the organic material in water to facilitate the particular industrial use or chemical reaction desired.

This is particularly so with organic compounds which are used for agricultural purposes, such as, herbicides, pesticides, and the like. Thus, such compounds are normally applied to the plants and/or the earth in which the plants are growing and the best means of transporting the material into the plant or the earth is through water transport. However, because of the insolubility of many of these compounds, it is necessary to formulate them into emulsions or dispersions, usually in the presence of appropriate surface-activating agents, e.g., surfactants, and the like. The formulation of such emulsions increases the expense and manpower in the utilization of these agricultural chemicals. In addition, very often the efficiency of transport into the ecological system is not as high as desired. The ability to dissolve compounds of this nature in water in high concentrations would represent a significant achievement in this area of use.

With respect to pharmaceutical compounds, water is, of course, the solvent of choice. Indeed, it is normally impossible to use organic solvents as carriers for pharmaceuticals because of the toxicity associated with organic materials or solvents. Moreover, with pharmaceuticals which are used either for oral or injectable dosages, it is desired to have a higher rather than a lower concentration in water, since this decreases the particular amount of the material needed in any given dosage. Often, however, it is extremely difficult to obtain any significant or effective degree of solubility of such compounds in water so as to enhance their pharmaceutical efficacy.

In the past, it has been known that the use of polyvinylpyrrolidone could be used to increase the rate of dissolution of certain organic compounds in water. However, this art does not relate to an increase in solubility, but rather, only to an increase in the rate of dissolution. See L. M. Mortada, "Effect of Polyvinylpyrrolidone and Urea on Dissolution Rate of Phenylbutazone from Solid State Dispersion", Sci. Pharm. 48, 241–247 (1980); O. I. Corregan, R. F. Timony and M. J. Whelan "The Influence of Polyvinylpyrrolidone on the Dissolution and Bioavailability of Hydrochlorothiazide", J.Phar. Pharmac. 28, 703 (1976); and R. Voight and D. Terborg, "Granulometric Determination of the Effect of PVP on Dissolution Rates of Sparingly Soluble Drugs", Pharmazie, 35, 311–312 (1980).

Numerous methods have been utilized for enhancing the solubility of complicated organic chemicals. For example, in U.S. Pat. No. 3,673,163, a method is described for the use of polyvinylpyrrolidone having molecular weights in excess of 1,000 by coprecipitating the polyvinylpyrrolidone with the drug Acronine. However, the increase in solubility obtained was only about 2.5 times the solubility of the compound. Such an increase in solubility for many of these compounds is not sufficient to render the use of the compound effective from a commercial or practical point of view.

Greater increases in solubility of highly insoluble organic compounds have been obtained as disclosed in application Ser. No. 106,845, filed Oct. 9, 1987. This has been accomplished by complexing the organic compound with a solid homopolymer or copolymer of N-vinyl-2-pyrrolidone having a molecular weight of greater than 1,000. In this method, solid N-vinyl-2-pyrrolidone and the organic solvent are first dissolved in a mutual solvent and the solution i subjected to a complexing reaction. Thereafter, the solvent is removed, leaving the water-soluble complex. However, in certain instances, specific organic compounds do not exhibit as high a water-solubility of the complex as might be desired.

SUMMARY OF THE INVENTION

We have discovered a method for substantially increasing the water solubility of highly insoluble organic compounds in the range of at least 25 times the solubility of the compounds alone as measured at 25° C. at atmospheric pressure. Indeed, we have discovered a method for increasing the solubility of such compounds in many cases in excess of 100 times their original solubility.

This is accomplished by forming a novel adduct product from the reaction between the organic compound and an oligomer of vinylpyrrolidone.

More particularly, the process of the invention can be carried out by suspending the organic compound in the pure vinylpyrrolidone polymer or an aqueous solution thereof. The suspension is then heated at a temperature and for a time period sufficient to produce a clear liquid or solution. The upper limit of the temperature is determined primarily by the thermal stability of the organic compound. Thus the temperature must be sufficiently low so as to avoid decomposition of the compound. If appropriate, the heating step may be carried out under an inert atmosphere. As used herein, the term "oligomer" means a polymer of vinylpyrrolidone containing from two to five monomeric units. The vinylpyrrolidone oligomer is a viscous liquid and has a molecular weight below 1000, and preferably, within the range from about 210 to 600. Preferably, an oligomer composed of from three to four monomeric units is used. The method of the invention is advantageous inasmuch as no mutual solvent is required and, consequently, there is no need to remove the solvent in order to obtain the complex. In addition, higher solubilities with certain compounds can be achieved as compared to the prior art complexes. Also, the complex exhibits substantial stability at room temperature.

DESCRIPTION OF THE PREFERRED EMBODIMENT

More specifically, the oligomers of the present invention may be prepared by one of several methods. Typically, for instance, a vinylpyrrolidone oligomer may be prepared by the cationic polymerization of vinylpyrrolidone. This is accomplished by the addition of an acid catalyst directly to vinylpyrrolidone. Typically, mineral acids, e.g. sulfuric acid, or Lewis acids, e.g., borontrifluoride, can be used. A procedure for the preparation of the oligomers is disclosed in German Examined Patent Application (Auslegeschrift) No. 1,040,031, published Oct. 2, 1958.

The adducts of the present invention may be prepared in several ways. The organic compound to be complexed may be suspended in the pure vinylpyrrolidone oligomer, an aqueous solution of the oligomer, or a buffered solution of the oligomer. Typical buffer solutions include phosphate buffer solutions, and the like. The pH of the buffer solution may be adjusted as desired, depending on the particular end use. Generally, a pH of from about 1 to 10 would be used.

Typically, the concentration of the oligomer in the aqueous or buffered solution is in the range from about 5% to 100%, and preferably, from about 30% to 100%. The suspension is then heated for a period of time sufficient to dissolve the organic compound and obtain a clear solution. Normally, this time period is from about 15 to 90 minutes, although it may take longer than this. The temperature of heating usually ranges from about 45° C. to 95° C. and is carried out with stirring.

The ultimate clear solution obtained exhibits a shelf life of a week or longer at ambient temperatures.

A wide variety of substantially water-insoluble organic compounds may be used for forming the complexes of the present invention. Such compounds are disclosed in U.S. Pat. No. 4,666,992, and copending applications Ser. Nos. 858,778, filed May 2, 1986; 858,635, filed May 2, 1986; 858,976, filed May 2, 1986; 849,918, filed Apr. 9 1986; 858,977, filed May 2, 1986; and 858,978, filed May 2, 1986, the disclosures of all of which are incorporated herein by reference.

As used herein, the expression "substantially insoluble" means that the solubility of the compound in water is so low as to render its use in aqueous solution impractical or highly inefficient, e.g., for insoluble pharmaceuticals.

In addition to the compounds disclosed in the above patents and/or copending applications, we have discovered that additional insoluble compounds may be treated using the present invention. In particular, those compounds which are especially adapted for hydrogen bonding, polar bonding, hydrophobic bonding, ionic bonding, and bonding by van der Waals forces are highly susceptible to a complexing with the oligomers utilized in the present invention to produce complexes exhibiting solubilities which are extremely high multiples of the solubility of the original organic compound.

The following examples illustrate the present invention:

EXAMPLE 1

A vinylpyrrolidone oligomer (VP) was prepared by the addition of concentrated sulfuric acid (0.3% based on VP) directly to VP over a period of 4 hours at 20–30° C. The final product had a K value of 7.9 with a residual VP content of less than 1%. The pH of a 5% aqueous solution of the VP oligomer is 2.6.

A 50% VP oligomer buffer solution was prepared by mixing 50 g of the VP oligomer with 50 g of an aqueous phosphate buffer (pH=6.95, ionic strength of 0.1). The pH was adjusted to 7.0 with sodium hydroxide solution.

Indomethacin, 0.04 g, was suspended in 4.0 g of the 50% VP oligomer buffer solution. The suspension was heated at 85° C. for 1.5 hours on a water bath with continuous stirring. The resultant clear indomethacin/VP oligomer solution was stable over a six day period. One part of the drug/polymer complex was diluted with three parts phosphate buffer (pH=6.95). The diluted solution was also stable for six days without precipitation. Since the original aqueous solubility of indomethacin is 0.0005%, a 4000-fold increase was achieved by complexation with the VP oligomer.

EXAMPLE 2

Dapsone (4-aminophenyl sulfone) (0.1 g) was suspended in 4.0 g of the 50% VP oligomer buffered solution (pH=7.0) of Example 1. The suspension was heated at 85° C. for 1.5 hours with continuous stirring. The resultant solution was clear and stable for over six days at room temperature.

EXAMPLE 3

Furosemide (0.1 g) was suspended in 4.0 g of buffered VP oligomer solution (pH=7.0) of Example 1. The drug/VP oligomer solution was heated at 85° for 1.5 hours. The clear solution was slowly cooled down to room temperature whereby a clear drug/polymer complex was formed which was stable for over six days. One part of the furosemide/VP oligomer was added to 9 parts of a phosphate buffer solution (pH=6.95). The diluted furosemide solution was stable without precipitation for over six days.

EXAMPLE 4

Chlorhexidine, 0.04 g, was suspended in 4.0 g of buffered 50% VP oligomer solution (pH=7.0) of Example 1. The drug/VP oligomer solution was heated at 85° C. for 1.5 hours. The aqueous drug solution was stable at room temperature for over 6 days. One part of the chlorhexidine/VP oligomer solution was added to 3 parts of phosphate buffer solution (pH=7.0). The diluted drug solution was stable at room temperature without precipitation for six days.

EXAMPLE 5

1 g of furosemide was mixed with 20 g VP oligomer as prepared in Example 1 at 80° C. for 1 hour, then slowly allowed to cool to room temperature to give a waxy solid material. When 1 g of this drug/VP oligomer complex was stirred in 1 g water, a clear solution resulted which was stable for at least one week.

What is claimed is:

1. An adduct of a substantially insoluble organic compound selected from the group consisting of indomethacin, dapsone, furosemide, and chlorhexidine and a liquid oligomer of N-vinyl-2-pyrrolidone, the water solubility of the adduct being at least about 25-fold that of the organic compound itself.

2. The adduct of claim 1 wherein the oligomer has a weight average molecular weight of less than 1000.

3. The adduct of claim 1 wherein the oligomer has a weight average molecular weight in the approximate range from about 210 to 6000.

4. The adduct of claim 1 wherein the oligomer is composed of 3 to 4 monomeric units.

5. The adduct of claim 1 wherein the ratio of insoluble compound to oligomer is from about 2 : 1 to 1 : 300.

6. The adduct of claim 1 having a water solubility of greater than about 100-fold that of the insoluble compound.

7. A method for preparing the adduct of claim 1 comprising preparing a suspension of an insoluble organic compound selected from the group consisting of indomethacin, dapsone, furosemide, and chlorhexidine in a liquid oligomer of N-vinyl-2-pyrrolidone, and heating the suspension at a temperature and for a period of time sufficient to dissolve the organic compound.

8. The method of claim 7 wherein the oligomer has a weight average molecular weight of less than 1000.

9. The method of claim 7 wherein the oligomer has a weight average molecular weight in the approximate range from about 210 to 600.

10. The method of claim 7 wherein the oligomer is composed of 3 or 4 monomeric units.

11. The method of claim 7 wherein the ratio of insoluble compound to oligomer is from about 2 : 1 to 1 : 300.

12. The method of claim 1 wherein the suspension is heated at a temperature in the range from about 45 to 95° C. for a period of time from about 15 to 90 minutes.

13. A method for preparing the adduct of claim 1 comprising preparing a suspension of an insoluble organic compound selected from the group consisting of indomethacin, dapsone furosemide, and chlorhexidine in an aqueous solution of a liquid oligomer of N-vinyl-2-pyrrolidone and heating the suspension at a temperature and for a time sufficient to dissolve the organic compound.

14. The method of claim 13 wherein the concentration of oligomer in the aqueous solution is from about 5 to 99 percent by weight.

15. The method of claim 13 wherein the oligomer is composed of 3 to 4 monomeric units.

16. The method of claim 13 wherein the ratio of insoluble compound to oligomer is from about 2 : 1 to 1 : 300.

17. The method of claim 13 wherein the oligomer has a weight average molecular weight of less than 1000.

18. The method of claim wherein the oligomer has a weight average molecular weight in the approximate range from about 210 to 600.

* * * * *